United States Patent [19]

Torre

[11] Patent Number: 4,944,739
[45] Date of Patent: Jul. 31, 1990

[54] BONE GRIPPING FIXATION CLAMP

[76] Inventor: Randall J. Torre, 842 S. Clover, San Jose, Calif. 95128

[21] Appl. No.: 328,494

[22] Filed: Mar. 24, 1989

[51] Int. Cl.$^5$ .............................................. A61B 17/56
[52] U.S. Cl. ...................................... 606/53; 606/207; 81/418
[58] Field of Search .................. 128/303 R, 305, 321, 128/346, 92 VZ, 322; 269/6; 81/418–420; 294/118; 433/157, 159; 606/157, 205, 206, 207, 120, 53, 105, 151

[56] References Cited

U.S. PATENT DOCUMENTS

| | | | |
|---|---|---|---|
| 97,399 | 11/1869 | Holmes | 81/418 |
| 2,253,132 | 8/1941 | Malson | 128/321 |
| 2,883,750 | 4/1959 | Haas | 81/418 |
| 3,503,397 | 3/1970 | Fogarty et al. | 81/421 |
| 4,031,624 | 6/1977 | Heimann | 433/159 |
| 4,197,647 | 4/1980 | Goldenthal | 433/159 |
| 4,475,544 | 10/1984 | Reis | 128/92 VZ |
| 4,655,223 | 3/1987 | Kim | 128/321 |

Primary Examiner—Michael H. Thaler
Assistant Examiner—William Lewis
Attorney, Agent, or Firm—Schroeder, Davis & Orliss Inc.

[57] ABSTRACT

A pliers-like clamping device having offset bone gripping plates temporarily grips and clamps together two bone segments above and below as diagonal cut at an osteotomy site. The device includes a pair of handle members having distal ends which are turned at substantially right angles to the handle arms and parallel to each other and offset both vertically and horizontally from each other. The distal ends form bone-gripping plates which may be serrated or ribbed on their inwardly facing surfaces. A ratcheting mechanism is provided near the proximal end of the device so that the clamping force may be set and maintained at a desired level.

7 Claims, 3 Drawing Sheets

BONE GRIPPING FIXATION CLAMP

BACKGROUND OF THE INVENTION

The present invention relates generally to surgical instruments and, more particularly, to clamps which are utilized during an osteotomy procedure.

In performing the surgical procedure widely known as osteotomy, a bone is divided or cut or a small piece or section of the bone is removed. Once the bone has been cut or the bone section removed, it is necessary to align the bone pieces in a desired configuration and join the pieces together and allow the bone pieces to grow back together. Typically, the bone pieces are temporarily clamped together utilizing a hand-operated clamping device and maintained in alignment at the osteotomy site while a permanent fixation procedure, such as the K-wire fixation or A-O techniques, is completed. At the conclusion of the fixation procedure, the clamping device is removed.

It is well-known in the prior art to provide bone-clamping apparatus for use during a surgical procedure. Typically, prior art devices utilize plier or forceps apparatus having opposed curved fingers or curved plate-like jaws to surround and grip a bone. The clamping pressure is manually applied by action of pivotable handles and is maintained by ratcheting handles or thumbscrew arrangements. U.S. Pat. Nos. 1,958,108 to Rush, 4,009,712 to Burstein et al and 4,201,215 to Crossett et al provide examples of prior art bone-clamping devices. A primary consideration in the design of surgical instruments is providing sufficient clearance around a temporary clamp to allow the performance of surgical procedures. Most of the prior art devices provided for surgical access by having handles which, when the clamp was installed, hopefully provided sufficient clearance for surgical procedures.

U.S. Pat. No. 4,475,455, entitled "Bone Gripping Forceps" issued to Reis, describes a scissors-like apparatus having the configuration of forceps with distal ends which are turned inwardly towards each other so that the distal ends are substantially collinear when the apparatus is being used as a bone clamp. The distal ends have sharp points which engage the bone to enable clamping pressure to be exerted between them and to allow the clamp to pivot out of the way of surgical procedures to be performed when the clamp is installed. While the clamp described by Reis is well suited for repair of bone fractures, collinear, sharpened distal ends do not maintain longitudinal alignment well and the sharpened ends tend to dig into the bone.

SUMMARY OF THE INVENTION

In accordance with the principles of the present invention, a bone-clamping device comprises an apparatus having a configuration similar to a pair of pliers and which has distal ends which are turned at substantially right angles to the plier arms and parallel to each other and offset both vertically and horizontally from each other. The distal ends form bone-gripping plates which may be serrated or ribbed on their inwardly facing surfaces. A ratcheting mechanism is provided near the proximal end of the apparatus so that the clamping force may be set and maintained at a desired level. With the offset bone-gripping plates, two bone segments at an osteotomy site may be clamped together, one plate gripping a bone segment above a diagonal cut and the other plate gripping the other bone segment on the opposing side and below the cut with the bone-gripping plates clear of the osteotomy site. In this manner, the bone segments may be temporarily clamped together to allow the performance of a further fixation procedure. The ratcheting mechanism is of sufficient dimensions to permit a wide range of plate openings and the ratchet teeth are closely spaced to allow minute adjustments in the level of clamping pressure when the clamp is applied. The bone clamp is fabricated from stainless steel and will be manufactured in two sizes.

DETAILED DESCRIPTION OF THE PREFERRED EMBODIMENT

Figure 1:
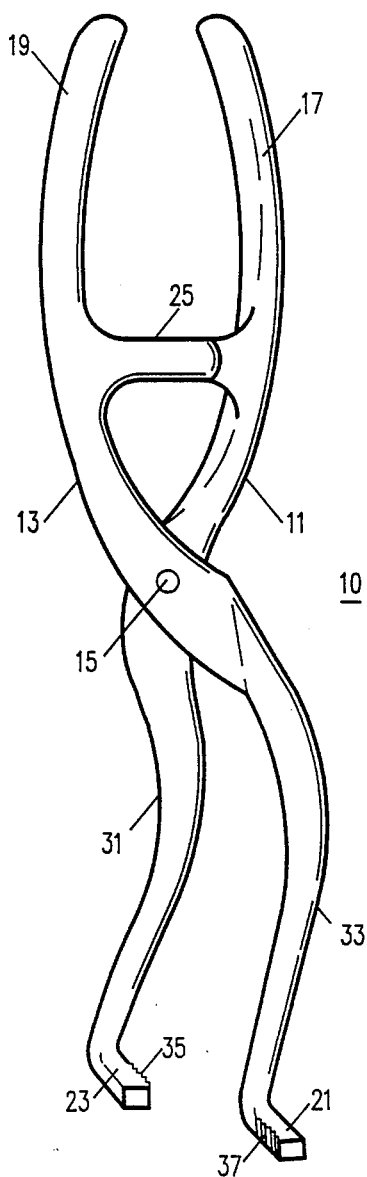
FIG. 1 is a perspective view of a bone clamp constructed in accordance with the principles of the present invention.
Figure 2:
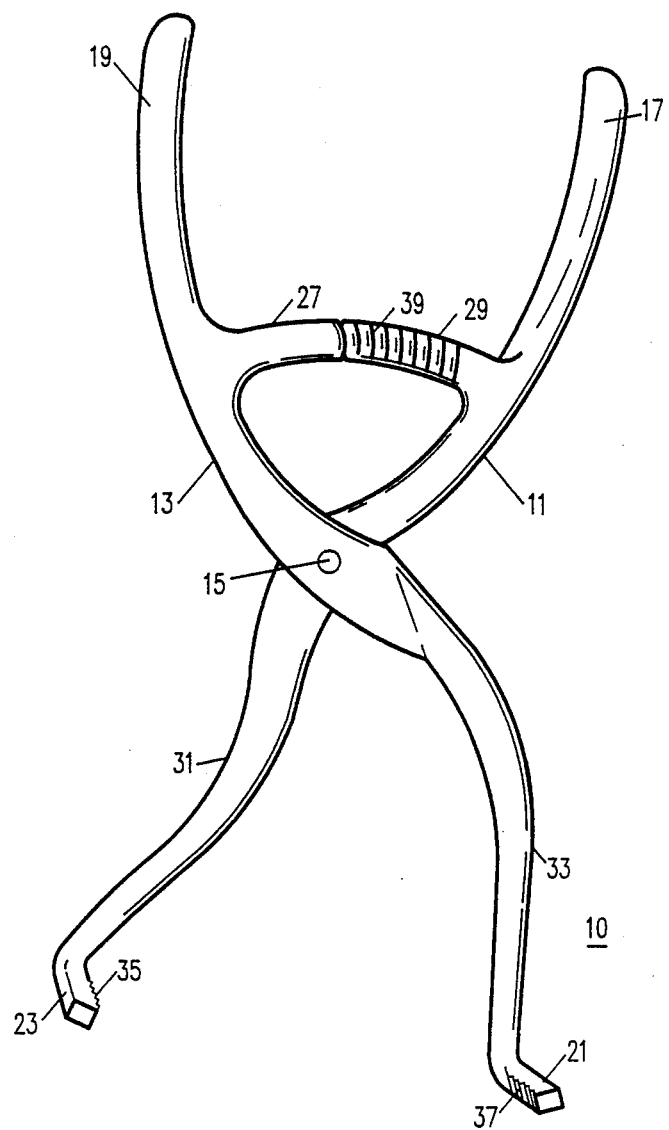
FIG. 2 is a perspective view of the bone clamp shown in FIG. 1 illustrating the ratchet mechanism.

Referring now to FIGS. 1 and 2, a bone clamp constructed according to the principles of the present invention is shown. The bone clamp 10 comprises a pair of longitudinal plier arms 11 and 13 which intersect approximately midway between their ends at a pivot bearing 15. The plier arms 11, 13 each have, at the proximal ends thereof, handle portions 17 and 19, respectively, and bone-gripping finger portions or plates 21 and 23, respectively, at the other, distal ends thereof. Intermediate the handle portions 17 and 19, is a ratcheting mechanism 25 comprising a ratchet arm 27 integral with one plier arm 13 and a ratchet catch 29 integral with the other plier arm 11.

Each of the bone-gripping finger portions 21, 23 is integral with its associated plier arm 11, 13, respectively, and is bent so as to be at approximately a right angle with respect to its associated plier arm. The finger portions 21, 23 are also turned so as to be approximately parallel to each other.

The finger portions 21, 23 are generally rectangularly shaped, their inwardly facing, opposing faces 35, 37 being serrated or ribbed to grip the bone surface. To facilitate the desired orientation of each finger portion 21, 23 with respect to each other, each plier arm 11, 13 has an intermediate lower arm portion 31, 33 respectively. The lower portion 31 of one plier arm 17 bends slightly outwardly and rearwardly while the lower portion 33 of the other plier arm 19 bends slightly outwardly and forwardly with respect to each other so that the finger portions 21, 23 are spaced apart a predetermined distance and offset both vertically and horizontally.

Figure 3:
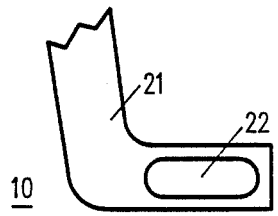
FIG. 3 is a side view in section of a second embodiment of the bone clamp bone-gripping plates constructed in accordance with the principles of the present invention.

Referring now also to FIG. 3, another embodiment of the bone clamp bone-gripping plates constructed according to the principles of the present invention is shown. The bone clamp 10 is constructed similarly as shown in FIGS. 1 and 2. Each of the bone-gripping finger portions or plates 21, 23 at the distal ends of the plier arms 13, 11, respectively, include an elongated hole 22 formed transversely through the finger portion 21, 23. The elongated hole 22 extends through the serrated face 35, 37 of the finger portions 23, 21, respectively, providing access to the bone surface when the bone clamp is being utilized (as shown in FIG. 6) to allow installation of a screw or other bone fixation hardware (not shown).

The ratchet mechanism 25 is formed in a well-known manner, the ratchet arm 27 and the ratchet catch 29 each having a series of ratchet teeth on their opposing faces in an engaging relationship. Engagement of the ratchet arm 27 and the ratchet catch 29 maintains the finger portions 21, 23 at the desired separation distance and clamping pressure when installed. The ratchet arm 27 and ratchet catch 29 will engage each other so as to prevent the handle portions 17 and 19 from separating until such time as a user applies a twisting movement substantially parallel to the axis of the pivot bearing 15 to lift the ratchet arm 27 away from the ratchet catch 29 thus disengaging the ratchet teeth 39. The ratchet teeth 39 are separated from each other by a fixed linear distance allowing the ratchet arm 27 to engage the ratchet catch 29 at as many discrete positions as there are ratchet teeth 39 providing an adjustable range of openings between the finger portions 21, 23. The plier arms 11, 13 have sufficient overlap with respect to each other at the pivot bearing 15 to minimize twisting of the finger portions 21, 23 when the ratchet mechanism 25 is being engaged or disengaged.

The plier arms 11, 13 are constructed to have sufficient flexibility to allow adjustability of the finger portions 21, 23 whenever clamping pressure is maintained over the entire range of the ratchet mechanism 25. The bone clamp 10 is constructed form a material having sufficient flexibility and corrosion resistance, such as stainless steel or other suitable material.

Figure 4:
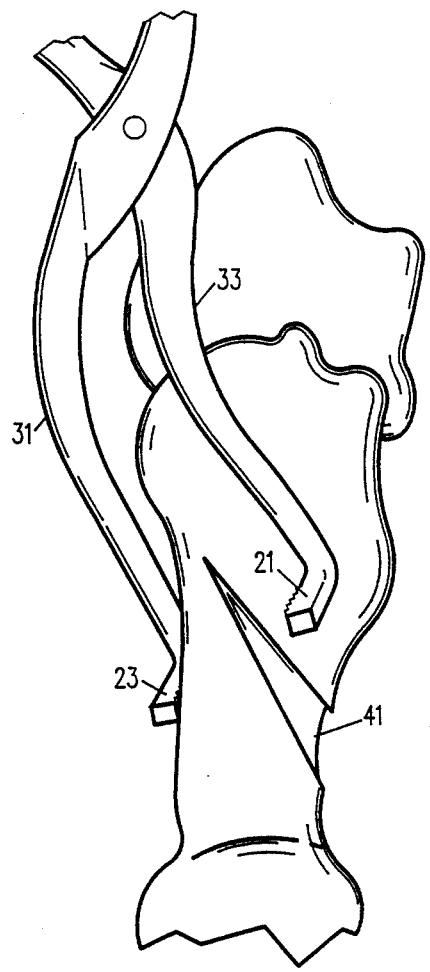
FIG. 4 is a perspective view of the bone clamp of FIG. 1 illustrating the use and positioning of the bone clamp prior to closing a long oblique wedge osteotomy.
Figure 5:
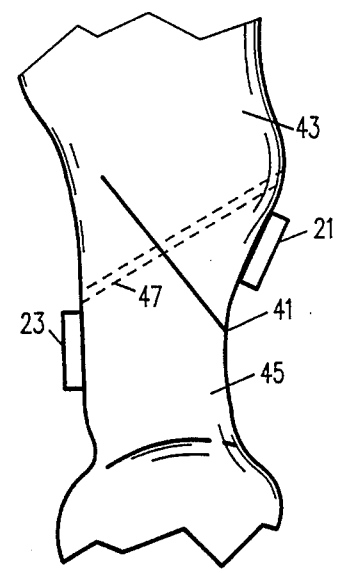
FIG. 5 is a side view of the bone clamp of FIG. 4 illustrating the bone clamp maintaining the bone segments in contact at the osteotomy site.
Figure 6:
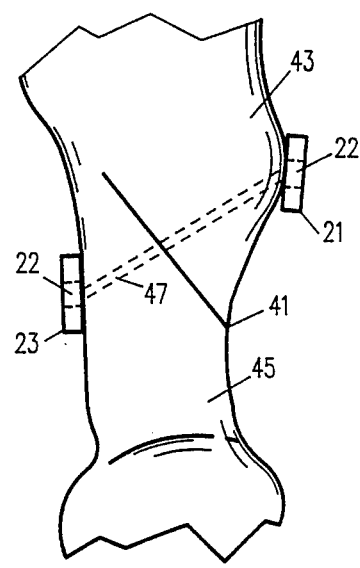
FIG. 6 is a side view of the bone clamp incorporating the embodiment shown in FIG. 3 illustrating the bone clamp maintaining the bone segments in contact at an A-O site.

Referring now also to FIGS. 4, 5 and 6, the bone clamp 10 is being used to temporarily clamp a pair of bone segments 43, 45 together at an osteotomy site 41 to facilitate further surgical procedures for permanent fixation. FIG. 4 illustrates the proper positioning of the finger portions 21, 23 and the associated lower arm portions 33, 31, respectively, above and below a long oblique wedge osteotomy site 41 at selected pressure points. In FIG. 5, clamping pressure has been applied by adjusting the ratchet mechanism 25 to the proper engagement point thereby urging the finger portions 21, 23 together and compressing the upper bone segment 43 against the lower bone segment 45 at the osteotomy site 41. Thus positioned, the bone clamp will maintain the bone segments 43, 45 in contact and in longitudinal alignment until the completion of a permanent or semipermanent fixation procedure, such as the A-O technique indicated by dashed lines 47. In FIG. 6, the finger portions 21, 23 of a bone clamp have been positioned over the opposite ends of a guide hole indicated by dashed lines 47 drilled during an A-O procedure and clamping pressure applied. Thus positioned, the bone clamp will maintain the bone segments 43, 45 in contact and longitudinal alignment while allowing the insertion of an A-O screw (not shown) through the hole 22 to complete the A-O procedure.

Although the present invention has been described in its preferred forms with a certain degree of particularity, it is understood that the present disclosure of the preferred embodiment has been by way of example and that numerous changes in the details of construction and the combination and arrangement of elements may be resorted to without departing from the spirit and scope of the invention as hereinafter claimed.

I claim

1. A bone clamp for clamping bone segments together at an osteotomy site, comprising:

a pair of elongated members, each of said elongated members having a handle portion formed at an upper end thereof and a lower portion;

pivot means medially interconnecting said pair of elongated members;

a pair of bone-gripping means, each of said bone-gripping means rigidly attached to said lower portion of a respective one of said elongated members, each said bone-gripping means extending from its respective elongated member at a predetermined angle oriented to be substantially parallel to and adjacent the other one of said pair of bone-gripping means, each of said lower portions bent away from the other lower portion such that each one of said pair of bone-gripping means is disposed in a facing, opposed relationship having a horizontal and vertical offset therebetween; and ratching means disposed between said elongated members disengagably coupling said handle portions together, said ratchet means having a plurality of discrete engagement points, each engagement point associated with a corresponding lateral separation between said pair of bone-gripping means, said ratchet means preventing said elongated members from rotating about said pivot means until said ratch means is disengaged.

2. The bone claim as in claim 1 wherein said bone-gripping means comprise generally rectangular-shaped finger portions, each of said finger portions having a flat, inwardly facing surface.

3. The bone clamp as in claim 2 wherein each of said rectangular-shaped finger portions include an aperture formed therethrough, said aperture extending transversely through each said finger portion and inwardly facing flat surface.

4. The bone clamp as in claim 3 wherein each said inwardly facing surface is serrated.

5. The bone claim as in claim 3 wherein each of said bone-gripping means is formed integrally with said lower portion of a respective one of said elongated members.

6. The bone clamp as in claim 5 wherein said bone clamp is fabricated of stainless steel.

7. The bone clamp as in claim 2 wherein each said inwardly facing surface is serrated.

* * * * *